United States Patent [19]

Watts

[11] Patent Number: 4,688,853

[45] Date of Patent: Aug. 25, 1987

[54] SHAPE-DEFINING ARTICULATED STRUCTURES

[76] Inventor: Robert J. Watts, 19 Pendarves Road, Wimbledon, London SW20 8TS, England

[21] Appl. No.: 824,267

[22] Filed: Jan. 30, 1986

[51] Int. Cl.$^4$ .............................................. A47C 7/02
[52] U.S. Cl. .................................... 297/459; 52/460; 297/284; 297/460
[58] Field of Search ............... 297/284, 459, 460, 458; 128/90; 403/143; 446/95, 121, 265; 404/35; 52/584, 659, 660; 24/265 C, 333, 335

[56] References Cited

U.S. PATENT DOCUMENTS

| | | | |
|---|---|---|---|
| 3,055,398 | 9/1962 | Tunnessen | 24/335 |
| 3,256,785 | 6/1966 | Stammbach et al. | 404/35 |
| 3,310,906 | 3/1967 | Clukes | 446/95 |
| 3,379,472 | 4/1968 | Hilfiker | 297/284 |
| 3,565,482 | 2/1971 | Blodee | 297/284 |
| 3,583,091 | 6/1971 | Brockway | 446/121 |
| 4,347,840 | 9/1982 | Adams | 297/284 |
| 4,367,897 | 1/1983 | Cousins | 297/284 |
| 4,484,778 | 11/1984 | Cousins | 297/458 |

FOREIGN PATENT DOCUMENTS 0018658 11/1980 European Pat. Off. .
0062448 10/1982 European Pat. Off. .

Primary Examiner—James T. McCall
Attorney, Agent, or Firm—Lowe, Price, LeBlanc, Becker & Shur

[57] ABSTRACT

An articulated structure for defining, when rendered rigid, a desired multi-curved surface, the structure being adjustable to permit the shape of the curved surface defined thereby to be varied at will. Such structures are particularly useful in the field of medical and other kinds of specialized seating, medical braces, and children's constructional toys.

The structure comprises an array of inter-connected, cooperating rings or links (12,28) and spiders (10). The radiating limbs of the spiders (10) have at or near their respective free ends jaw or other clamping means (22,24) in which cooperating parts (26) of the rings (12) are clamped by screw or other clamping means (18). The shape of the array is adjustable by relaxing the clamping means (18) of selected spiders (10) and then retightening them after the desired shape has been achieved by displacing the relevant members (10,12) of the array.

13 Claims, 27 Drawing Figures

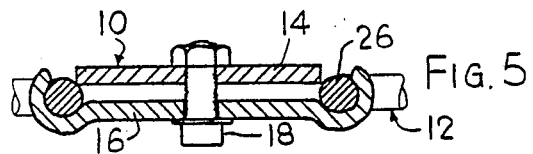
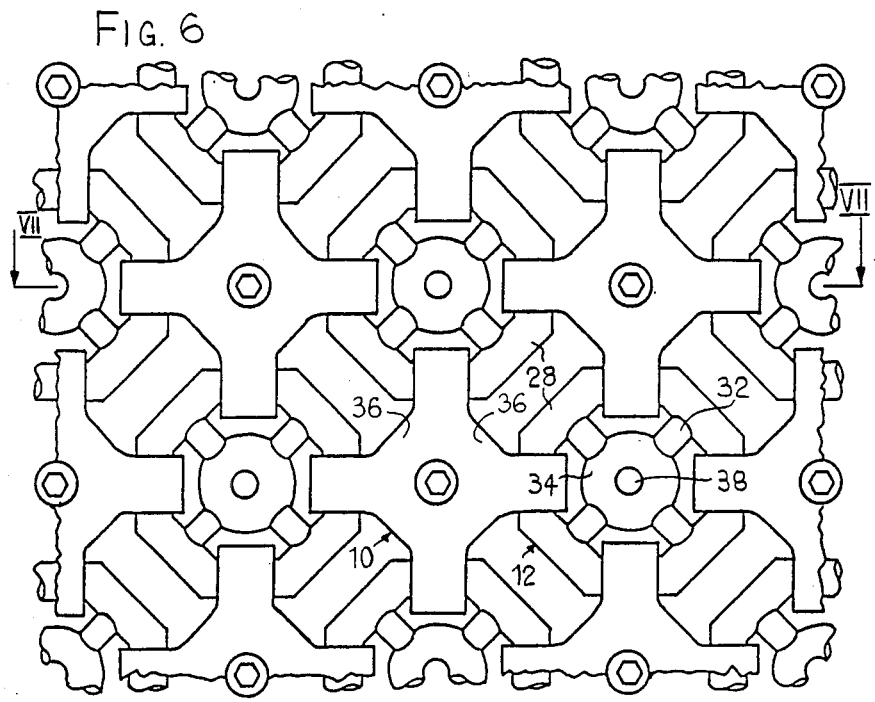
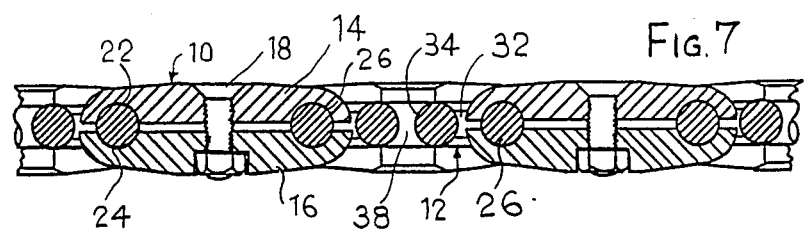
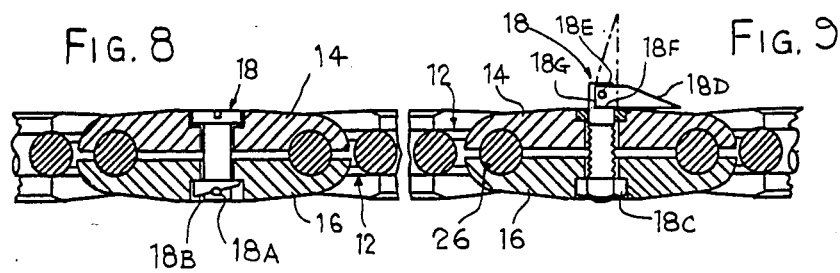

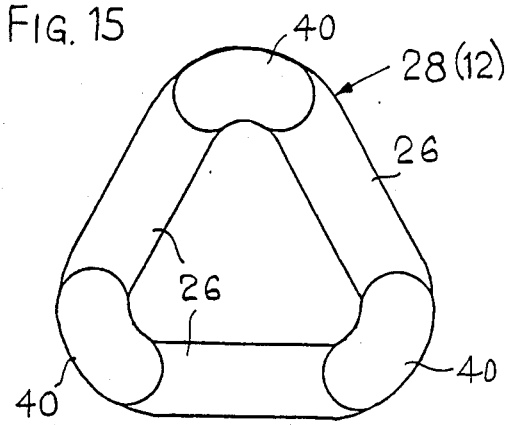
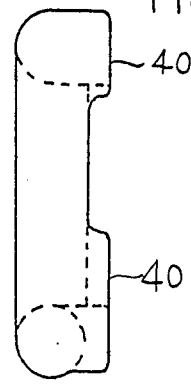
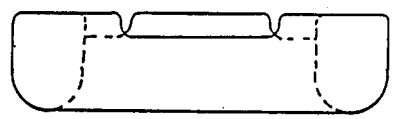
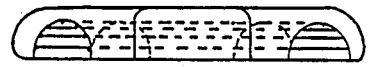
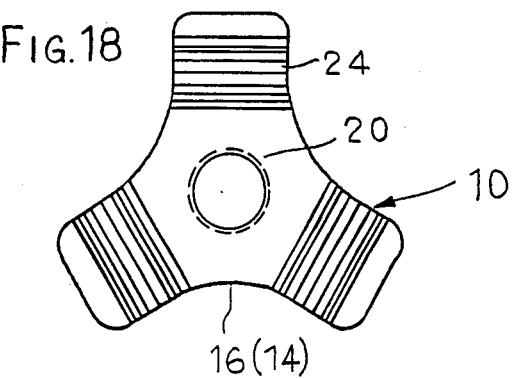

SHAPE-DEFINING ARTICULATED STRUCTURES

TECHNICAL FIELD

This invention relates to an articulated structure for defining, when rendered rigid, a desired multi-curved surface, said structure being adjustable to permit the shape of the curved surface defined thereby to be varied at will.

Such structures are particularly useful in the field of specialised seating, as for example for use in racing cars, aircraft and space vehicles; in chairs and vehicles for deformed or disabled people; and in body braces for supporting fractured, deformed or weakened bones or bone systems.

BACKGROUND ART

One such shapeable articulated structure has been described in the European patent publication No. 0062448 A1 (EPC Appl'n. No. 8231533.4). In that document, each described structure comprises an array of inter-connected first and second elements, the elements of one such kind being provided with clamping means for engaging and clamping parts of at least two adjoining elements of the other kind, and the said array being rendered rigid by tightening the respective clamping means. It has been found in practice that articulated structures as described in that publication have certain disadvantages which it is desirable to obviate; thus, it is desirable to provide a lighter, stronger, more flexible articulated structure that is more versatile in its fields of application, that is more simply secured in a seat frame, and that is more resiliently flexible in use.

DISCLOSURE OF THE INVENTION

According to one aspect of the present invention, an articulated structure of the kind referred to in the preceding paragraph is characterised in that:

each said first element has radiating from a central portion thereof a plurality of circumferentially spaced arms, each such arm being provided at or near its free end with a said clamping means for engaging and clamping when desired a part of an adjoining second element, and each said second element comprises a link (preferably, closed upon itself) having a plurality of clamping portions each of which is arranged to be received in and clamped by a said clamping means, each said clamping means being arranged so that when in a relaxed condition the said link engaged thereby may pivot relative to the associated first element about an axis that is common to both the plane of that first element and the plane of that engaged second element.

Preferably, each said clamping means is constituted by a pair of jaws, one of which is formed by the associated arm of said first element, and means for moving at least one said jaw of said pair relative to the other whereby to close and open that pair of jaws.

In one preferred arrangement according to the present invention each said first element comprises a pair of cooperating, opposed, similar half members, each such half member comprising a plurality of arms radiating from a central portion and being urged towards the opposed half member by a common clamping means disposed in said central portion, and each pair of cooperating opposed arms of said half members constituting a said pair of jaws.

Each said first element may conveniently have between two and eight of said radially-projecting arms, each incorporating a said pair of jaws; and said radially-projecting arms may be equi-spaced, or non-equi-spaced as described. Furthermore, said pairs of jaws may all be positioned equi-distantly from a central point of a said first element, or they may be set at different distances from said central point as desired. Said first elements, and likewise said second elements, may in the same array be of different sizes and/or shapes according to the needs of the shape of the surface to be defined by the structure.

The said links may be circular in configuration, or they may be polygonal, having conveniently no more than eight sides; and links of different configurations may be used in the same array. Preferably, each portion of a link that is to be engaged in a pair of said jaws is shaped in a manner that is complementary to that of the jaws. Alternatively, a malleable adaptor may be provided for accommodating any difference in the shapes of the jaws and the parts of the links to be received in the jaws.

The jaws of each pair may be arranged to exert a clamping force on an engaged portion of a said link in a direction that is normal to a central plane of the said first element carrying those jaws. Alternatively, said jaws may be arranged to exert a force in a direction that is radial relative to a central point on the said first element.

According to a second aspect of the present invention, there is provided an adjustable seat frame for carrying an articulated structure according to the present invention, which seat frame is provided in its various limb members with pivotal and/or telescopic adjustment means whereby the frame may be readily adapted, within wide limits, to the physical dimensions and desired attitude of a said articulated structure that has been fitted to the shape of a specific person, and which seat frame incorporates fixing means whereby the said articulated structure may be securely fixed on that frame after appropriate adjustment of the frame to suit that structure.

According to a further aspect of the present invention, a body brace comprises a plurality of shaped articulated structures according to the present invention, which structures are aligned and connected together side by side, and are shaped to support and/or restrain a specific body or body part, the connection of at least one such structure to the adjacent one being releasable at will, and the other connection(s) of adjacent structures being hingeable, whereby on release of the said releasable connection the brace may be opened, the said structures being hingeable apart to allow the brace to be placed around or removed from the said body or body part. The hingeable connections may comprise pivoted connections, or they may comprise flexible connections.

Other features of the present invention will appear from the description that follows hereafter, and from the claims appended at the end of that description.

One adjustable, self-supporting, shape-defining articulated structure according to the present invention, various modifications of and alternatives to that structure, and adjustable seat frame for carrying such an articulated structure after it has been shaped to the form of a disabled person, and a spinal body brace will now be described by way of example and with reference to the accompanying diagrammatic drawings.

BRIEF DESCRIPTION OF THE DRAWINGS

FIG. 5 shows in another transverse cross-section similar to that of the FIG. 2 a part of yet another modified form of the said structure;

FIGS. 6 and 7 show in views similar to those of the FIGS. 1 and 2 respectively a portion of a modified form of the articulated structure shown in the FIGS. 1 and 2;

FIG. 8 and 9 show in views similar to that of the FIG. 7 two modifications of the structure shown in the FIG. 7;

FIGS. 15, 16 and 17 show respectively front, side and inverse plan views of a said second element as used in the said alternative form of structure of FIG. 14;

FIGS. 18, 19 and 20 show respectively front, side and plan views of a said first element as used in the said alternative form of structure of FIG. 14;

For the convenience of the reader, in the description that follows, corresponding parts in the respective embodiments bear the same or closely related references.

DESCRIPTION OF EMBODIMENTS OF THE INVENTION

Figure 1:
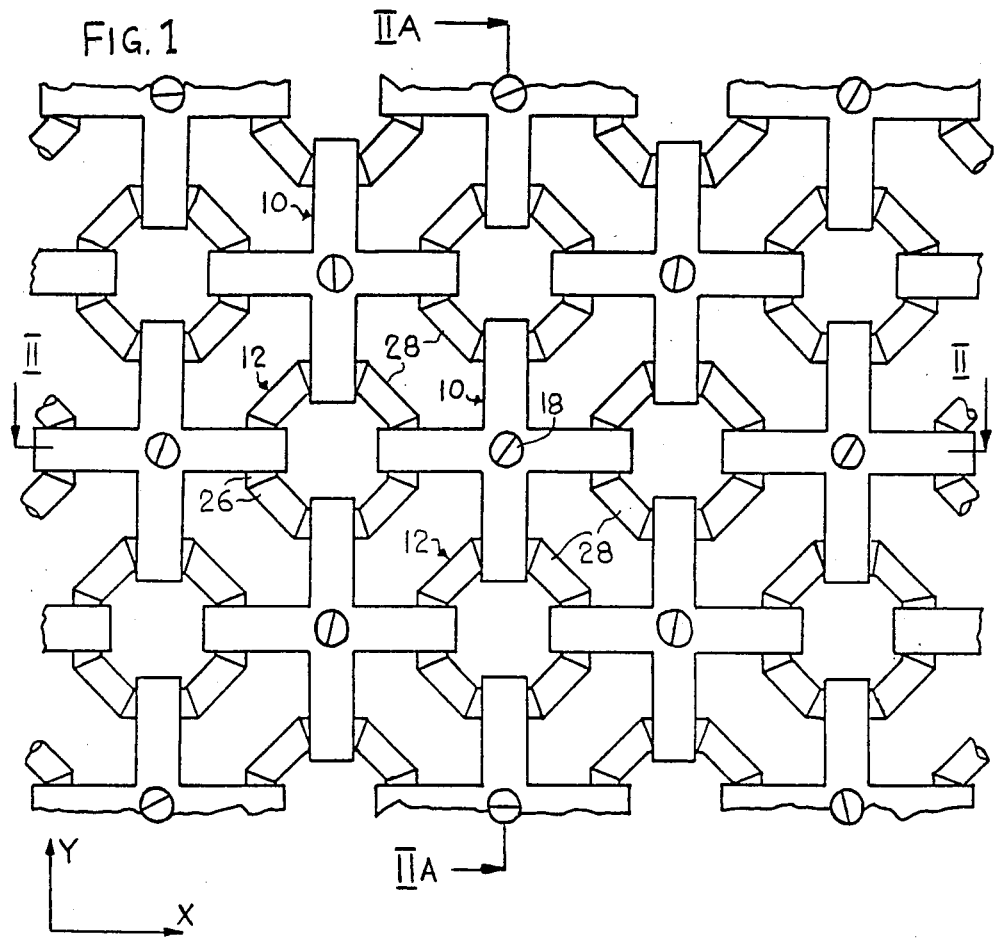
FIG. 1 shows a plan view of a portion of said structure when set to define a continuous planar surface.
Figure 2:
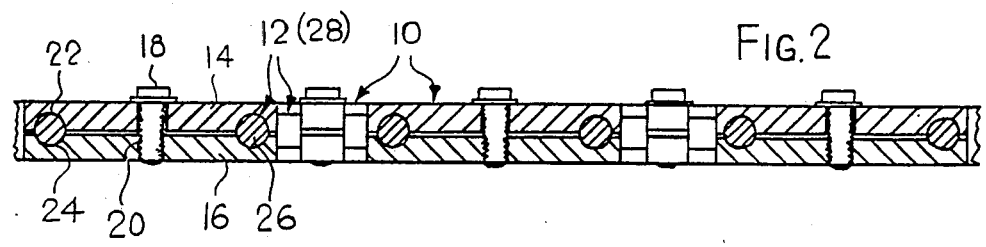
FIG. 2 shows a transverse cross-section taken on the section line II—II of the FIG. 1, that section line being aligned in the X direction as indicated therein.

Referring now to the FIGS. 1 and 2, the structure there depicted comprises an interconnected array of said first elements 10 and said second elements 12. Each said first element 10 is constituted as a two-part cruciform member comprising, as shown in the FIG. 2, cooperating upper and lower cruciform clamping members 14, 16 secured together centrally by a clamping screw 18, which is received in a tapped hole 20 formed in the lower clamping member 16, and which when tightened urges the two clamping members together. Those clamping members constitute at the ends of their radially-projecting arms respective pairs of jaws. Each such pair of jaws is provided with jaw or clamping grooves 22, 24, in which are received clamping portions 26 of four octagonal links 28 which are all operatively associated with the cruciform member 10. Those links constitute typically the said second elements 12 of the said structure.

In each such link 28, each straight portion 26 thereof is of circular transverse cross-section, has a suitably roughened cylindrical outer surface, and constitutes a clamping portion of the link. The jaw grooves of each cruciform clamping member 14, 16 are likewise rendered rough in a suitable manner so as to ensure a good grip on a clamping portion of a link when received therein. Roughening of said clamping surfaces on said links and in said jaw grooves may be achieved by causing said surfaces to be provided with knurling, serrations or silicon or other grit impressed therein.

The octagonal links are secured immovably in the associated cruciform members 10 when the associated clamping screws have been suitably tightened, so that the planar configuration illustrated in the Figures is substantially maintained even when the structure is subjected when in use to disturbing load forces.

To modify the shape of the continuous surface defined by the structure, for example—to cause it to conform to the shape of a person who is to be supported by the structure in a chair or vehicle, all or selected ones of the clamping screws 18 are slackened so as to enable relative angular displacement of appropriate cruciform members 10 and their associated links 28. By this means a limited variation of the shape of the structure can be achieved. In order to achieve greater variation of that shape, it is necessary to replace selected ones of said four-armed cruciform members by other said first elements 10 which have different numbers of angularly-spaced radial arms and jaws, or even by replacing selected links 28 with links of other configurations or sizes. Such other links may be, for example, of rectangular, triangular or even circular configuration. Links which are not wholly closed may be used in appropriate circumstances, for example links in the shape of the letter C or Z. However, these are not preferred, since closed links have greater strength.

The cruciform members 10 and the associated links 28 may be made of any suitable metal or plastics material.

Figure 3:
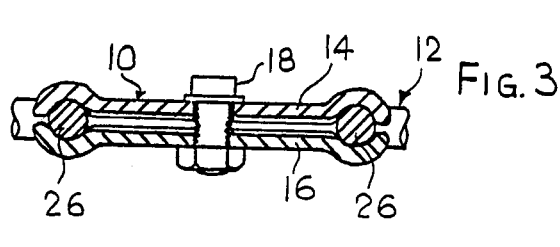
FIG. 3 shows a transverse cross-section similar to that of the FIG. 2, showing part of a modified form of said structure.

FIG. 3 shows an alternative form of said cruciform members 10 for use in the structure of FIG. 1, in which alternative form the cruciform member is composed of clamping members which have been stamped out from a suitably thin metal sheet. The radial arms of the two clamping members are cambered to provide strength.

Figure 4:
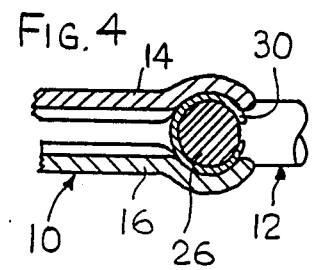
FIG. 4 shows a modification of part of the structure shown in FIG. 3.

In the FIGS. 1 to 3, the respective pairs of jaws compress the associated clamping portions of the respective links in directions which are essentially normal to the planes of the respective cruciform members. By way of contrast, the alternative form of cruciform member shown in the FIG. 5 has its constituent clamping members shaped to compress the clamping portions of the associated links in radial as well as normal directions. In that arrangement, the lower clamping member is provided with hooked end portions at the ends of its respective radial arms, in which portions the clamping portions of the respective links 28 are received. The upper clamping member has shorter radial arms, and the ends of those arms press, with line contact, on the outer parts of the said clamping portions of the links.

Where links 28 of circular or other curved configuration are used, it may be necessary to provide adaptors to accomodate the difference in shape of the clamping portions of the links 28 and the jaw grooves of the cruciform members 10. Such adaptors may take the form of thin, malleable, open shells which are interposed between the said clamping portions and the jaw grooves. Such a shell is shown in the FIG. 4 which shows only the relevant parts of the cruciform member 10. The shell is referenced 30.

Instead of using clamping screws for causing said jaws to grip the associated parts of the links 28, a rotary camming device or a toggle device may be used instead to provide a quicker means of locking and unlocking the cruciform members 10 on the associated links 28.

It will be appreciated that after adjusting the shape defined by the structure, that new shape is preserved in the structure by tightening all the clamping screws that had been released for adjustment purposes.

It will be appreciated that the transverse cross-section depicted in the FIG. 2 is also the transverse cross-section taken along a section line IIA—IIA in the Y direction indicated in the FIG. 1.

Instead of, or in addition to, roughening the cylindrical clamping surface of each clamping portion 26 of the links 28, each such clamping portion may advantageously be provided with a multi-facetted or toothed clamping surface, the clamping grooves in the respective cruciform clamping members being shaped correspondingly, or otherwise, as desired so as to provide a good clamping action on the links 28.

Referring now to the alternative form of structure shown in the FIGS. 6 and 7, that structure is generally similar to that described above with reference to the FIGS. 1 and 2, with the principal differences (a) the ring elements 28 (12) are cross-braced by spokes 32 (of circular transverse cross section) which radiate from a central ring portion 34 (likewise of circular transverse cross section);

(b) the clamping screw 18 of each said cruciform first element 10 has a countersunk head and engages with an hexagonal nut, which is likewise coutersunk, so as to provide a relatively smooth contour to each side of the structure;

(c) the cruciform members 14 and 16 constituting each said first element 10 are strengthened by web portions 36 which fill the corner spaces between adjacent jaw arms;

(d) the holes 38 formed in and by the ring portions 34 constitute holes for fixing the structure at desired positions to a supporting seat frame and for securing an interface or upholstered seat cover to the structure whereby to provide comfortable sitting to the user of the seat;

(e) each ring element 28 (12) has only four instead of eight clamping positions.

Whereas in the embodiment shown in the FIGS. 6 and 7, each said second element 12 (28) has four radial spokes 32, in an alternative embodiment only two such spokes are present.

Figure 10:
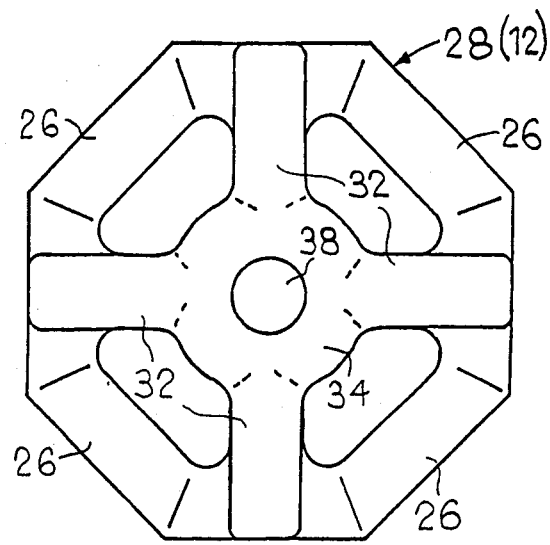
FIGS. 10 and 11 show respectively front and side elevations of a said second element as used in one form of the said modified form of structure illustrated in the FIGS. 6 and 7.
Figure 11:
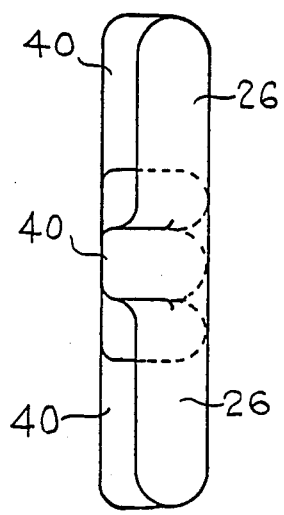

The construction illustrated in the FIGS. 6 and 7 is particularly suited to the use of a plastics material such as polypropelene or nylon. An alternative construction more suited to the use of a metal is illustrated in the FIGS. 10 to 13. The ring element 28 shown in the FIGS. 10 and 11 is provided with strengthening ribs 40 which are intended to stand up on the side of the structure that is to receive the upholstery seat cover, and so give a more uniform surface for receiving that cover.

Figure 12:
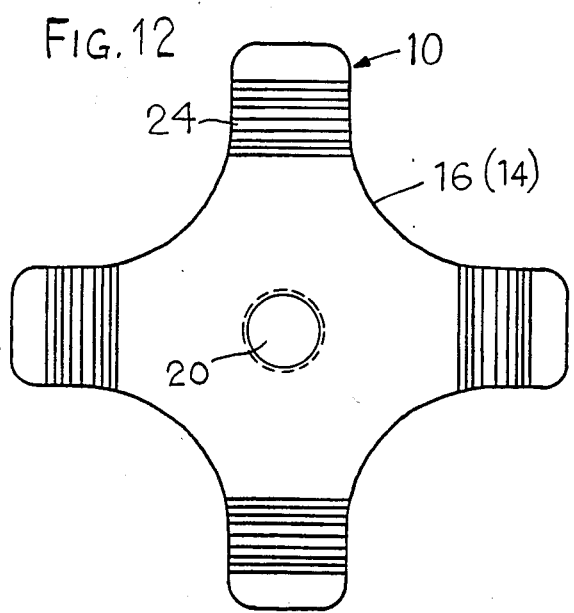
FIGS. 12 and 13 show respectively front and side elevations of a said first element as used in one form of the said modified form of structure illustrated in the FIGS. 6 and 7.
Figure 13:
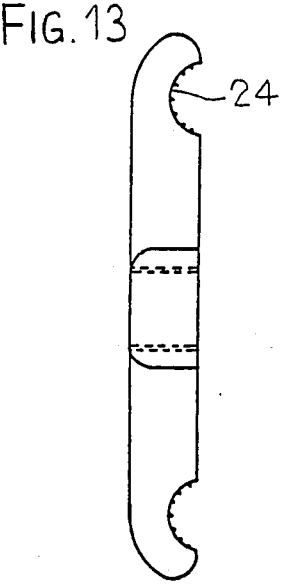
Figure 14:
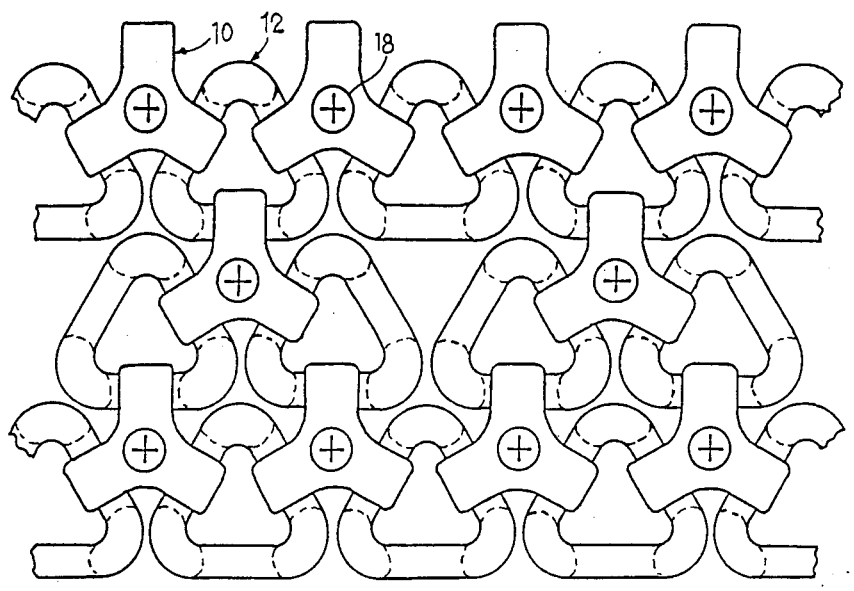
FIG. 14 shows in a plan view a portion of a said alternative form of said structure.

Each cruciform clamping member 16 is, as shown in the FIGS. 12 and 13, provided with a central screw-threaded hole 20, and toothed clamping grooves 24.

Those clamping members are intended to lie adjacent the said seat cover. Each clamping member 14, as shown in the FIGS. 12 and 13, is substantially the same as its couterpart 16, with the exception that it is provided with a central, countersunk clearance hole for receiving the head of the clamping screw 18.

Instead of using the normal, slow-acting rotation of an ordinary clamping screw 18 to clamp or relax each pair of clamping members 14 and 16, quicker acting clamping devices may be used instead, for example, a rotary camming device as shown in the FIG. 8, or a toggle device as shown in the FIG. 9.

In FIG. 8, a clamping 'screw' 18 carries at its lower, free end a double-ended transverse pin 18A which cooperates with two angularly spaced, arc-shaped wedges 18B to draw the clamping members 14 and 16 together quickly by means of a mere half-turn of the screw 18, for example, by means of a coin-edge inserted in a wide screw-driving slot formed in the head of the screw.

In FIG. 9, a headless clamping 'screw' 18 engages in the normal way in a countersunk clamping nut 18C, and is provided at its opposite end with a toggle lever 18D which is pivoted on a transverse pin 18E secured in the shank of the clamping screw. The lever 18D is provided with two camming surfaces 18F and 18G which define a knuckle and enable the lever to be positioned stably atlernatively in an upright, released position (shown in dotted form), with the clamping members 14 and 16 relaxed on the associated clamping portions 26 of adjacent ring elements 12 (28), or in a horizontal, clamped position, with those clamping members clamping the associated ring elements by virtue of the greater distance of the camming surface 18F from the pin 18E.

In an alternative articulated structure shown in the FIGS. 14 to 20, each of the said first elements 10 is generally Y-shaped, and has only three uniformly-spaced, radially-projecting, jaw-carrying clamping arms. Likewise, each of the links 28 constituting a said second element 12 has only three clamping portions 26, and is of triangular shape. Like the clamping members shown in the FIGS. 10 to 13, the said first and second elements of the present structure are intended for manufacture from a metal, such as a light aluminium alloy, each such clamping member 16 being provided centrally with a screw-threaded hole 20, and each such cooperating member 14 being provided centrally with a cooperating countersunk clearance hole.

Figure 21:
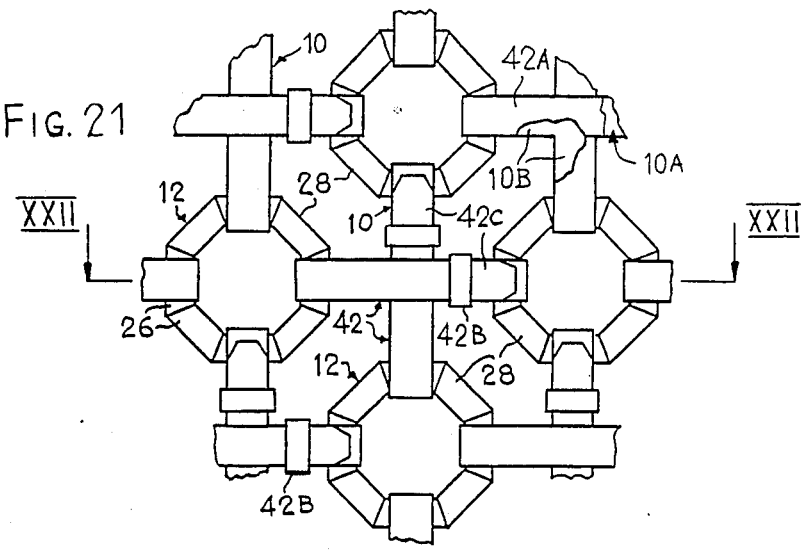
FIGS. 21 and 22 show a portion of a further alternative to the said structure illustrated in the FIGS. 1 and 2, FIG. 21 being a plan view (as in the case of FIG. 1), and FIG. 22 being ( as in the case of FIG. 2) a section on the plane indicated in the preceding figure.
Figure 22:
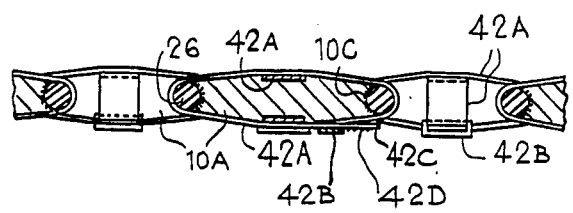

In yet another embodiment of the present invention shown in the FIGS. 21 and 22, (that embodiment being a modification of that shown in the FIGS. 1 and 2), each said first element 10 is constituted by a solid cruciform member 10A having four equi-spaced arms 10B of equal length, each such arm having at its extremity a serrated or toothed clamping surface 10C. Those surfaces abut against the adjacent clamping portions 26 of the adjacent links 28 (12), and are held tightly in clamping contact therewith by a releasable tie member 42 of the kind that is commonly used for tying together bundles of electric cables. Each such tie member comprises a thin elongate strap 42A of a suitable plastics material, at one end of which is formed an arch 42B through which the other, free end 42C of the strap can be threaded and drawn tight. Transverse teeth 42D formed at spaced positions on the strap cooperate with a releasable catch carried in the arch 42B to prevent release of the free end of the strap except when the said catch is deliberately moved from its engaging position to its disengaging position.

Figure 23:
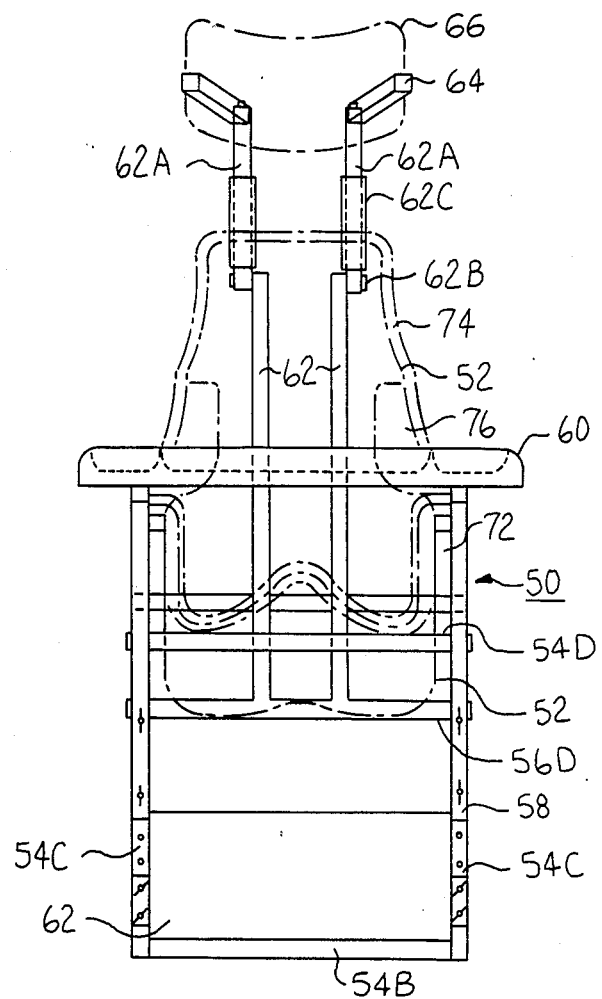
FIGS. 23, 24 and 25 show respectively front, side and plan views of said seat frame.
Figure 24:
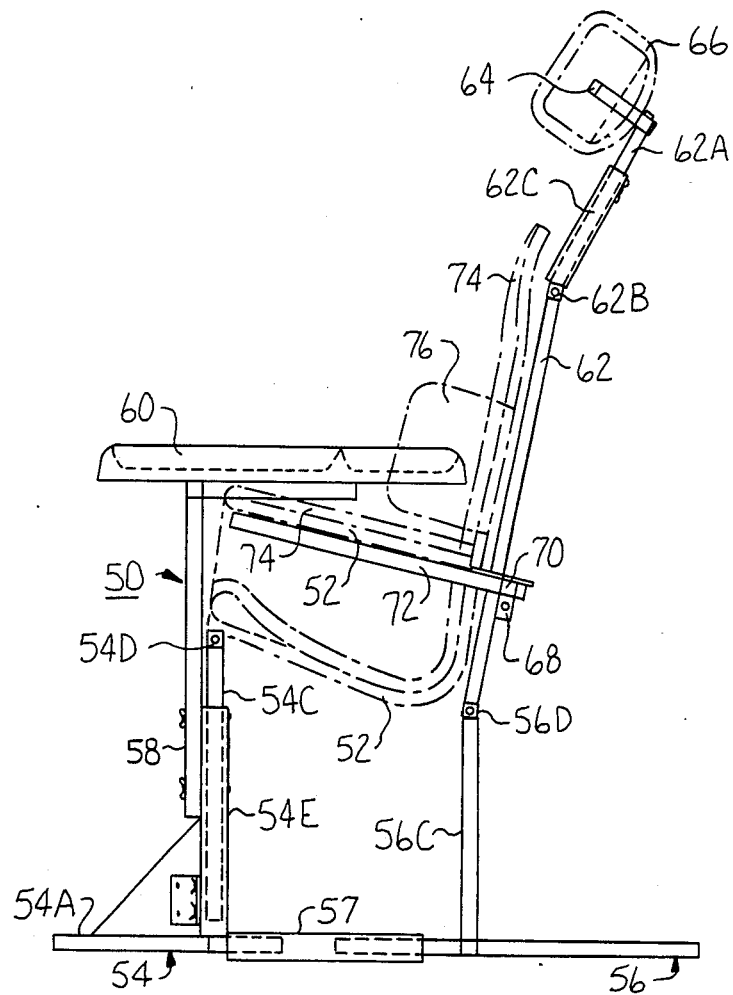
Figure 25:
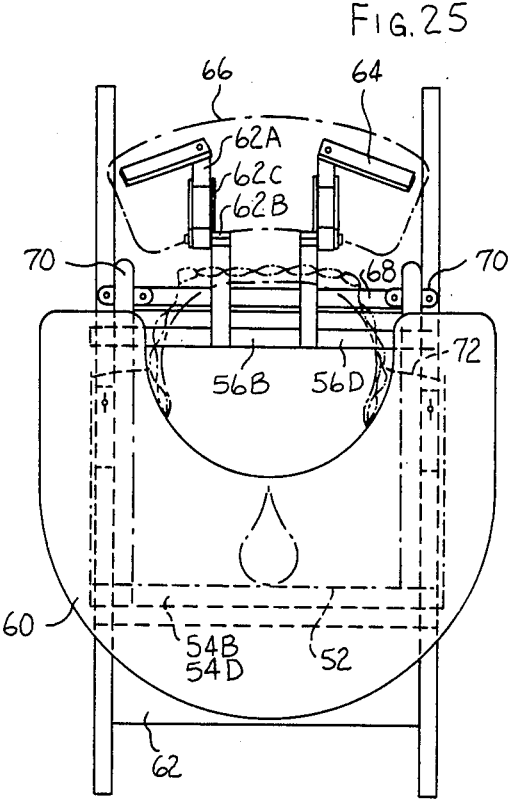

Referring now to the FIGS. 23 to 25, there is shown there a seat frame 50 for receiving and supporting a rigid, shape-defining articulated structure 52 according to the present invention, which structure has been shaped to a particular person's contour. The seat frame is composed principally of tubular metal members, the principal ones of which are provided with adjustment means to enable the shape and configuration of the seat frame to be adjusted within a wide range.

The base of the frame comprises front and rear base portions 54 and 56 connected by a pair of adjustable telescopic connections 57. Each such base portion comprises a pair of longitudinal tubular members 54A, 56A inter-connected by a transverse tubular member 54B, 56B, and supporting a pair of upright tubular members 54C, 56C. The upper ends of those upright members are inter-connected by a transverse tubular member 54D, 56D. In the case of the front base portion, the upright members incorporate telescopic adjustment means 54E, so as to provide a means for readily adjusting the height of the transverse support member 54D.

Secured to the front faces of the upright members of the front base portion by screws and wing nuts are (a) tray support members 58 which carry on their upper transverse portions a tray 60, and (b) a foot support 61 comprising base, upright and two triangular side plates.

In the case of the rear base portion, the transverse member 56D carries centrally two transversely spaced tubular upright back support members 62, the upper portions 62A of which include pivotal connections at 62B, and telescopic adjustment means at 62C, and carry head-rest support members 64 for receiving an upholstered head-rest 66 (shown in chain-dotted form for simplicity's sake.

A transverse tubular member 68 secured adjustably to the lower portions of the back support members 62 carries at the respective ends thereof a pair of stirrups 70 which have elongated upper parts and which support a pair of side support members 72.

The said rigid, articulated structure 52 is secured to the seat frame by nut and bolt fixings which extend through apertures (such as the apertures 38) in the articulated structure and apertures formed in the tubular members of the seat frame. For simplicity's sake, the articulated structure is likewise indicated in the figures by chain-dotted lines. The articulated structure is provided with an upholstered seat covering 74 (also indicated in the figures by chain-dotted lines) to render the seat comfortable to the user, and if necessary that structure and seat covering may be provided with side wings 76.

Figure 26:
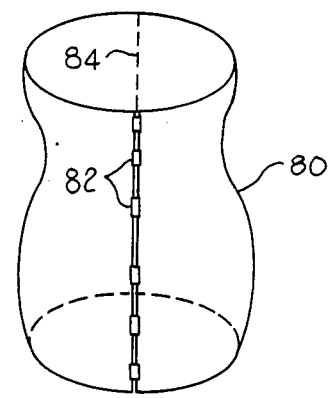
FIGS. 26 and 27 show pictorial views of a spinal body brace in the 'closed' and 'open' conditions respectively.
Figure 27:
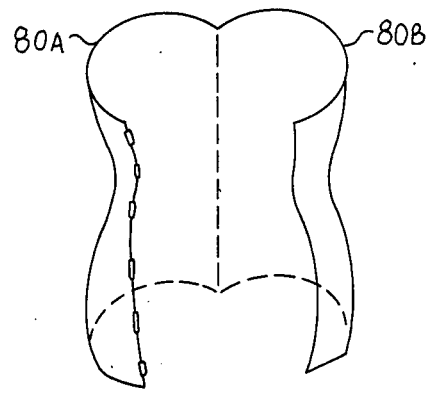

Referring now to the FIGS. 26 and 27, there is shown there a body brace 80 for a person requiring mechanical support for overcoming deformation of or deficiencies in the spinal column of that person. The brace comprises a rigid, shaped articulated structure according to the present invention, for example, of the kind illustrated in any of the Figures referred to above, the structure having been wrapped around and shaped to the person's body, and rendered rigid in that shape. The brace structure is provided with a vertical row of releasable catches 82 along the vertical front margins, and is sub-divided at the rear by a vertical row of spaced hinges 84 which connect adjacent portions of the structure.

On release of the said catches, the two hinged portions 80A, 80B of the brace can be hinged apart at the rear to enable the brace to be opened and to be placed in position around or be removed from the wearer's body.

If desired, the brace may be further sub-divided by providing other rows of hinges, so as to give greater flexibility.

The hinges may comprise hinges of the kind in which one hinge member pivots freely on another, or of the kind in which hinging is achieved by the flexing of a flexible hinge member. A hinge of the pivoting kind may be formed by enlarging slightly the aperture defined by the clamping grooves 22, 24 of a said first element 10, thus permitting the associated clamping portion 26 of an adjacent link element 28 (12) to pivot in that aperture.

Braces constructed on the same principles may be made for supporting a limb, such as a leg. Whatever the function of a brace constructed according to the present invention, it may be provided with a lining or interface for improving the comfort and/or support for the wearer.

The articulated structures described above may have spider (first) elements 10 and link (second) elements 12 of the same material, and that material may comprise a suitable plastics material or a suitable metal. Alternatively, the articulated structures described above may, if desired, used spider elements 10 of metal in combination with link elements 12 of a plastics material. In any case, it is preferred that the link elements 12 be made of a material that is softer and/or more resilient than that of the spider elements 10, so as to permit a good positive clamping action on the link elements 12 to be obtained.

The use of a thermo-plastics material for the link and/or the spider elements has the advantage that the shape of any such link or spider element can be changed by heating, deforming, and subsequently cooling that element. This provides greater flexibility in applying the structure to any particular desired shape or form.

In the embodiment of the FIGS. 21 and 22, the tie member 42 may incorporate fibre reinforcement in the plastics material. Alternatively, the tie member may be made of a suitable metal.

The articulated structures described above have the following advantages, as compared with the cited prior art structures, namely (a) the ring elements 28 (12) import a desirable degree of flexibleness into the structure, thus leading to greater comfort for the user;

(b) the ring elements are easily coupled and uncoupled from the clamping jaws of adjacent first elements 10;

(c) the manner of cooperation of the said first and second elements 10 and 12 enables a lighter structure to be produced, without loss of strength, adjustability, or adaptability to differing shapes; and (d) such structures are readily secured to a supporting framework.

Articulated structures according to the present invention, for example, those described above with reference to the various figures, may be used in children's constructional toys, for providing shaped curved surfaces for different purposes, and on different occasions.

I claim:

1. An adjustable, articulated structure for defining, when rendered rigid, a desired multi-curved surface, which structure comprises an array of inter-connected first and second elements, each of said first elements being provided with clamping means for engaging and clamping respective parts of at least two adjoining ones of said second elements, and the said array being rendered rigid by tighting the respective clamping means, characterised in that each said first element has radiating from a central portion thereof a plurality of circumferentially spaced arms, each such arm being provided at or near its free end with a said clamping means for engaging and clamping when desired a part of an adjoining second element, and each said second element comprises a link having a plurality of clamping portions each of which is arranged to be received in and clamped by a said clamping means, each said clamping means being arranged so that when in a relaxed condition the said link engaged thereby may pivot relative to the associated first element about an axis that is common to both the plane of that first element and the plane of that engaged second element.

2. An articulated structure according to claim 1, wherein each said clamping means is constituted by a pair a of jaws, one of which is formed by the associated arm of said first element, and means for moving at least one said jaw of said pair relative to the other whereby to close and open that pair of jaws.

3. An articulated structure according to claim 2, wherein wherein each said first element comprises a pair of cooperating, opposed, similar half members, each such half member comprising a plurality of arms radiating from a central portion and being urged towards the opposed half member by a common clamping means disposed in said central portion, and each pair of cooperating opposed arms of said half members constituting a said pair of jaws.

4. An articulated structure according to claim 3, wherein the respective half members of a said first element have formed in their respective arms circumferentially extending jaw grooves for receiving and clamping respective clamping portions of second elements.

5. An articulated structure according to claim 3, wherein said common clamping means comprises a screw-threaded nut and screw device.

6. An articulated structure according to claim 3, wherein said common clamping means comprises a quick-acting device constituted by a headed screw extending through both said half members and having near its free end a transverse pin which is arranged to ride over at least one arcuate, wedge-shaped cam, which cam is fixed in the said half member remote from the head of the screw, and the screw being rotatable relative to both half members and being drawn axially in a clamping direction by the said cam as the screw is rotated to cause said pin to ride around said cam.

7. An articulated structure according to claim 3, wherein each said common clamping means comprises a quick-acting device constituted by a screw shank extending through both said half members into a nut secured in one said half member, said screw shank carrying near its free end on a transverse pivot pin a toggle lever having cam surfaces shaped for engaging the half member disposed remotely from said nut, said lever being moveable between alternative stable unclamped and clamped positions, and said cam surfaces being shaped to draw said half members together whereby to clamp said clamping portions of adjoining elements as said lever is moved to said clamped position, and to relax said half members and thereby release said clamping portions as said lever is moved to said unclamped position.

8. An articulated structure according to any preceding claim, wherein each said link is provided with cross bracing members.

9. An articulated structure according to claim 8, wherein said cross bracing members radiate from a central annular portion which defines a fixing aperture for receiving a fixing screw or other device.

10. An articulated structure according to claim 1, wherein each said first element has formed at the end of each of its respective arms a clamping surface for engaging a said clamping portion of a said link, and wherein there is provided a releasable tie or strap for engaging around a said clamping portion when engaged with a said clamping surface whereby to clamp said clamping portion to said arm.

11. An articulated structure according to claim 1, in combination with an adjustable seat frame secured to and arranged for carrying and supporting said articulated structure, which seat frame comprises a plurality of articulated structure-supporting limb members connected together, at least some of which limb members incorporate adjustment means arranged for enabling adustment of the limb members relative to one another whereby to adapt the configuration of the seat frame to the shape of the articulated structure, which shape has first been adapted to the shape of a specific object or person to be received in and supported by said structure and its supporting frame, and at least some of said limb members incorporating fixing means for fixedly engaging respective ones of said elements of said shaped structure in said seat frame whereby to secure said articulated structure to said seat frame.

12. An articulated structure according to claim 1, in combination with at least one other similar articulated structure, each such structure having each of its respective opposite margins aligned with and connected to a complementary margin of an adjacent one of said articulated structures, the respective structures being adjusted so as to closely embrace and support a specific body or body portion, and at least one such articulated structure being provided at one of said margins with releasable connecting means adapted to releasably engage an adjacent margin of an adjacent one of said articulated structures, and at least one such articulated structure being provided at an opposite one of said margins with hingeable connecting means for hingeably connecting that margin with an adjacent margin of an adjacent one of said articulated structures, the arrangement being such that on release of said releasable connecting means one said structure may be hinged apart from an adjacent such structure, so as to allow the assembly of structures to be placed around or removed from a said body or body portion.

13. An articulated structure according to claim 12, wherein the or each said hingeable connecting means is formed by enlarging the said apertures defined by the said clamping means on selected arms of selected first elements of the respective adjoining structures, so as to enable the clamping portions of adjoining second elements engaged in said apertures to rotate in those apertures.

* * * * *